(12) United States Patent
Vogler et al.

(10) Patent No.: US 8,733,934 B2
(45) Date of Patent: May 27, 2014

(54) INSTRUMENT FOR EXAMINING OR MACHINING A HUMAN EYE

(75) Inventors: Klaus Vogler, Eckental (DE); Mario Abraham, Burgthann (DE)

(73) Assignee: Wavelight GmbH, Erlangen (DE)

( * ) Notice: Subject to any disclaimer, the term of this patent is extended or adjusted under 35 U.S.C. 154(b) by 0 days.

(21) Appl. No.: 13/108,307

(22) Filed: May 16, 2011

(65) Prior Publication Data

US 2012/0293772 A1 Nov. 22, 2012

(51) Int. Cl.
*A61B 3/00* (2006.01)
*A61B 3/14* (2006.01)

(52) U.S. Cl.
USPC .................................. 351/209; 351/200

(58) Field of Classification Search
USPC .......... 351/200, 205, 206, 208–211, 221, 222
See application file for complete search history.

(56) References Cited

U.S. PATENT DOCUMENTS

| | | | |
|---|---|---|---|
| 5,632,742 A | 5/1997 | Frey et al. | |
| 5,644,642 A | 7/1997 | Kirschbaum | |
| 7,480,396 B2 | 1/2009 | Teiwes et al. | |
| 8,050,504 B2 * | 11/2011 | Everett et al. | 382/218 |
| 8,465,477 B2 | 6/2013 | Donitzky et al. | |
| 2005/0024586 A1 | 2/2005 | Teiwes et al. | |
| 2005/0119642 A1 | 6/2005 | Grecu et al. | |
| 2006/0187462 A1 | 8/2006 | Srinivasan et al. | |
| 2010/0110376 A1 * | 5/2010 | Everett et al. | 351/206 |
| 2010/0211054 A1 * | 8/2010 | Lemonis | 606/5 |
| 2011/0032479 A1 * | 2/2011 | Utsunomiya | 351/206 |
| 2011/0144628 A1 | 6/2011 | Vogler | |
| 2012/0172853 A1 | 7/2012 | Riedel et al. | |

FOREIGN PATENT DOCUMENTS

| | | | |
|---|---|---|---|
| JP | 2000-237168 * | 2/1999 | A61B 5/117 |
| WO | 99/65431 A1 | 12/1999 | |
| WO | 02064031 A2 | 8/2002 | |
| WO | 03/070090 A2 | 8/2003 | |
| WO | 03/105678 A2 | 12/2003 | |
| WO | 2012110051 A1 | 8/2012 | |

OTHER PUBLICATIONS

Jungwirth et al., "Extended in vivo anterior eye-segment imaging with full-range complex spectral domain optical coherence tomography"; JBO Letters; Journal of Biomedical Optics; vol. 14. No. 5; pp. 050501-1-050501-3 (Sep./Oct. 2009).

Gora et al.; "Ultra high-speed swept source OCT imaging of the anterior segment of human eye at 200 kHz with adjustable imaging range"; Optics Express; vol. 17; No. 17; pp. 14880-14894 (Aug. 17, 2009).

Grulkowski et al.; "Anterior segment imaging with Spectral OCT system using a high-speed CMOS camera"; Optics Express; vol. 17; No. 6; pp. 4842-4858 (Mar. 16, 2009).

* cited by examiner

*Primary Examiner* — Joseph P Martinez
*Assistant Examiner* — Brandi Thomas

(57) ABSTRACT

An instrument is proposed for examining or machining a human eye, with an eye-tracker for acquiring eye movements and for outputting a signal that is representative of the acquired eye movements, the eye-tracker including an interferometric image-acquisition device that has been set up for time-resolved acquisition of sectional images of the eye and that operates on the basis of two-dimensional or three-dimensional optical coherence tomography, and also an evaluating module ascertaining the eye movements solely from the sectional images.

4 Claims, 3 Drawing Sheets

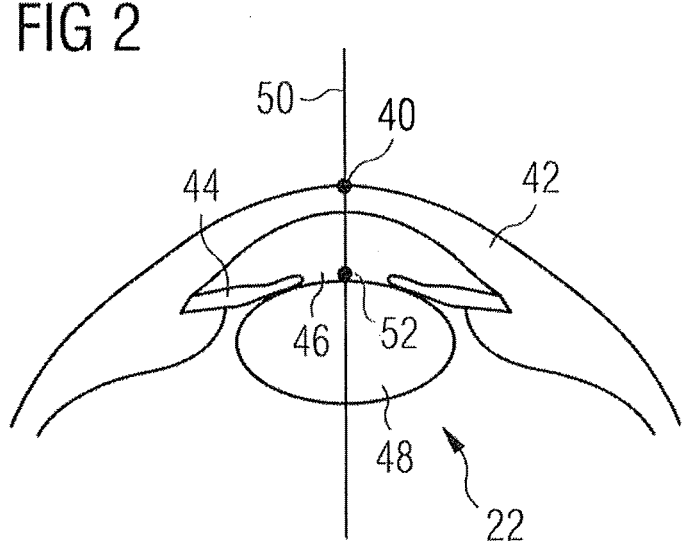
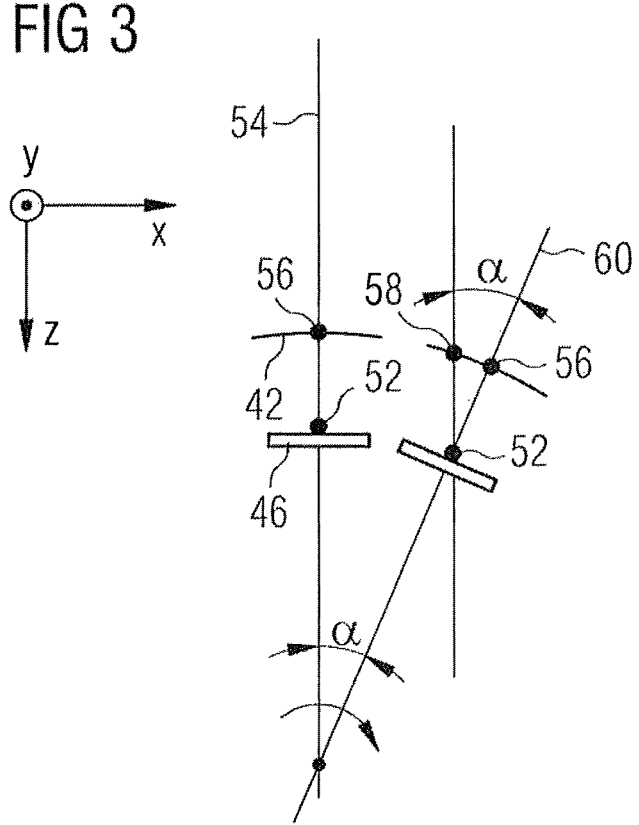

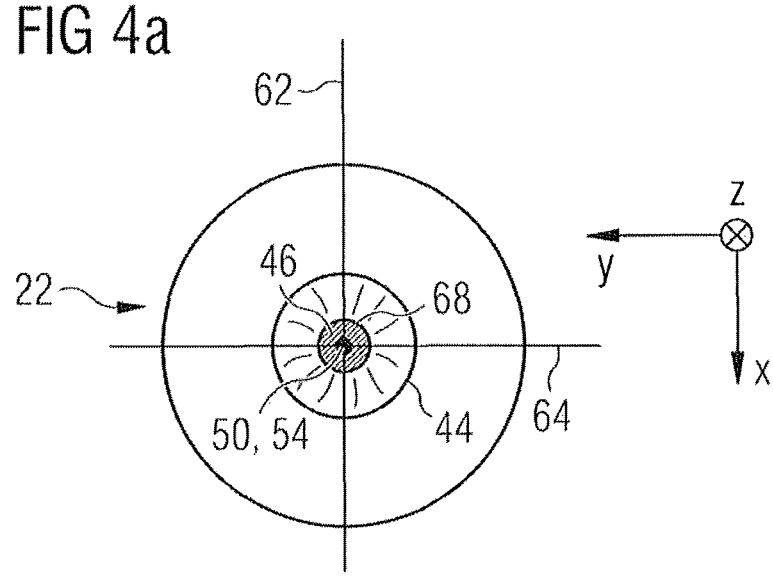
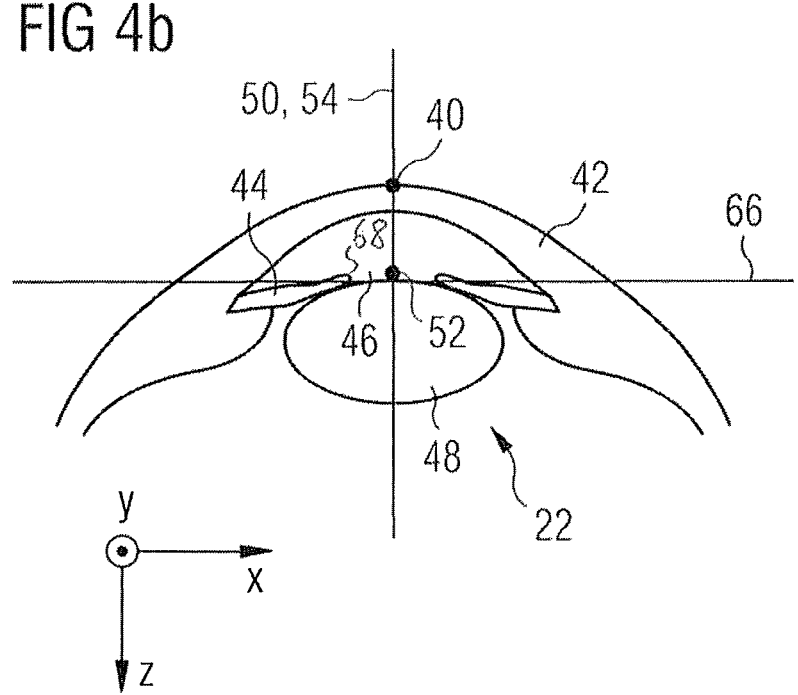

INSTRUMENT FOR EXAMINING OR MACHINING A HUMAN EYE

The invention relates to an instrument for examining or machining a human eye.

BACKGROUND OF THE INVENTION

Laser radiation is used in numerous techniques for treatment of the human eye. In some of these techniques focused laser radiation is utilised for the purpose of ablating (resecting) eye tissue. In this case it is necessary to direct the beam focus onto the eye in controlled manner, so that the ablation takes place at the desired position on the eye. But by virtue of movements of the eye during the treatment the eye may change in its position in relation to the treatment laser beam. This may then result in a discrepancy between a specified position and an actual position of the ablation.

For this reason it is desirable to track the movements of the eye and to take them into account in the control of the beam focus. For the purpose of acquiring the eye movements, use is made of an eye-tracker. At present, a two-dimensional eye tracking is generally conventional, which is based on the acquisition of the pupillary margin of the eye by only one camera. From the light/dark jump in contrast at the pupillary margin (iris), the pupillary centre is calculated which then serves as orientation coordinate for the laser ablation. Control of the treatment laser radiation is then effected by taking into account the position of the pupillary centre ascertained by the eye-tracker. However, the position of the pupillary centre does not always lie on the axis of symmetry of the eye or on the optical visual axis of the patient (for example, by virtue of asymmetrical displacement of the pupillary centre in the case of varying pupillary size, or deviation from circular symmetry in many patients). Such a deviation may result in suboptimal treatment outcomes.

In order to avoid such inaccuracies in the laser treatment resulting from the shift of position of the pupillary centre, the tracking of the pupil can be supplemented by a tracking of the limbus, which is oriented with respect to the invariable light-dark transition of the white sclera (sclerotic coat of the eye) to the iris. Prominent displacements of the pupillary centre can consequently be detected and taken into account in the ablation program as a so-called pupilcentre-shift correction (PCSC).

Overall, for the purpose of tracking the eye movement (eye tracking) the state of the art has hitherto utilised two-dimensional camera-image acquisition. Positional defaults derived therefrom may, however, be faulty, since the actual eye movements take place in three-dimensional space and consequently three translational movements as well as three rotational movements have to be described. Furthermore, eye-trackers that are based on camera-based two-dimensional image-recordings enable only the indirect acquisition of three-dimensional data by computationally intensive reconstruction. Meanwhile, camera-based eye-trackers have become available that enable a fivedimensional or six-dimensional eye tracking. In this connection, by an additional projection onto the eye of a pattern of light consisting of fringes and by the acquisition of these fringes (registration of the curvature, position and deformation of the fringes), a locational position and orientational position of the eye are inferred. But, here too, the registration process is intensive in terms of computation and time. Therefore the image-rate of eye-trackers used hitherto is limited in its speed and is often too slow for a correction of position in the course of the treatment of the eye with laser light. In addition, the camera systems utilised for this purpose merely detect light that has been scattered or reflected by the eye of the patient, which is why it is necessary to ensure appropriate illumination of the eye (which, however, may also have a disturbing effect on the treatment) and at the same time to avoid incidence of light from other secondary illuminations from the room onto the eye.

BRIEF SUMMARY OF THE INVENTION

It is an object of the invention to make available an instrument for examining or treating a human eye, said instrument including an eye-tracker that can provide results about eye movements with great speed and precision.

With a view to achieving this object, in accordance with the invention an instrument is provided for examining or treating a human eye, with an eye-tracker for acquiring eye movements and for outputting a signal that is representative of the acquired eye moments, the eye-tracker including an interferometric image-acquisition device that has been set up for time-resolved acquisition of sectional images of the eye and that operates on the basis of three-dimensional optical coherence tomography, and also an evaluating module ascertaining the eye movements solely from the sectional images.

The interferometric image-acquisition device may, for example, be characterised by a scan rate of >200,000 line scans per second, wide lateral scan ranges >=15 mm, depth ranges >8 mm to 12 mm, digital high-speed cameras (CCD, CMOS) with up to 12,000 pixels per line or more, high read-out speeds of about 140 kHz, high detection sensitivities of >−90 dB, and high resolutions within the range from <1 μm to 10 μm. Three-dimensional image-rates with 500 frames per second or more are possible.

The invention has the advantage that through the use of the interferometric measuring method the incidence of light from other secondary illuminations from the room onto the eye does not have a disturbing effect on the eye tracking, since only coherent light, but not incoherent light, enters into the measuring process.

The invention makes it possible, in addition, to use the high resolution, the high measuring speed and also the high sensitivity of interferometric image-acquisition devices that operate on the basis of three-dimensional optical coherence tomography not only, as hitherto, for the purpose of tomography, i.e. for structural surveying of a particular portion of the eye, but also for the purpose of measuring the position and the orientation of the eye in space. In this connection it is crucial that for the ascertainment of the position signals, orientation signals and movement signals only data from (one or more) interferometric image-acquisition devices are drawn upon that in each instance enable an image acquisition with assignment of X-, Y- and Z-coordinates to each image point.

With the aid of the time-resolved acquisition of the sectional images of the eye it is consequently possible to ascertain corresponding eye movements. Eye movements of such a type include cyclotorsional movements (flat rotations about the optical axis of the eye), rolling movements (rotations of the eye about an axis perpendicular to the optical axis of the eye) and also translational movements in all three directions in space. By reason of the use of the interferometric image-acquisition devices, the accuracy of measurement of the six-dimensional eye movements may be distinctly higher than that of an eye-tracker based on cameras. Similarly, the instrument according to the invention offers a distinctly higher speed in connection with the acquisition of the eye movements.

According to a further development of the invention, the interferometric image-acquisition device may have been set up to acquire at least two mutually orthogonal sectional images of the eye that each represent a section substantially along the visual axis of the eye. The sectional images may, however, also extend along the visual axis of the eye, parallel to the visual axis of the eye, or substantially along the central (optical) axis of the eye, along the central axis of the eye, parallel to the central axis of the eye, or oriented with respect to the apex of the eye. The two sectional images arranged mutually orthogonally permit an acquisition of orientations and positions and also of rolling and translational movements in the X- and Y-directions (in this connection the conventional notation is to be understood, in which the direction of propagation of the measuring beam of the interferometric image-acquisition device runs along Z, and X and Y jointly with Z complete the three-dimensional Cartesian coordinate system). A translational shift and/or translational movement in the Z-direction can also be determined from sectional images of such a type. The acquisition may, for example, be effected by a comparison with one or more sectional images determined previously (for instance, prior to the start of treatment). In particular, for this purpose highly resolved three-dimensional complete sectional images may be drawn upon for the purpose of comparison.

Furthermore, the interferometric image-acquisition device has preferentially been set up to acquire at least one sectional image of the eye that represents a section substantially along the margin of the iris of the eye. On the basis of this sectional image, prominent structures (for example, within the iris) can then be identified and can be utilised for a determination of the cyclotorsion of the eye. A section of such a type can consequently be understood as a faceon recording of the eye.

The interferometric image-acquisition device and the evaluating module have preferentially been set up to acquire a plurality of sectional images of the eye in time-resolved manner and to ascertain from the sectional images a time-resolved topography of a subregion of the eye as the signal that is representative of the eye movement. The plurality of sectional images of the eye may, for example, correspond to cross-sections of the eye that are offset parallel to one another. The subregion of the eye may, for example, entirely or partly include the cornea, the human lens, the anterior-chamber region, the sclera, the iris, the apex of the cornea, the centre of the lens of the human lens and/or the fovea.

The invention consequently makes it possible, on the basis of the time-resolved topography of the subregion of the eye (e.g. on the basis of the time-resolved topography of the cornea), to acquire translational and rotational movements of the eye and at the same time to orient a treatment of the eye with respect to an arbitrary point within the subregion (e.g. the apex of the cornea). The arbitrary point may be any outstanding feature of the subregion of the eye. This makes it possible to choose an outstanding feature of the subregion of the eye, on the basis of which a particularly exact orientation and precise implementation of a concrete treatment of the eye is possible. Accordingly it makes sense, for example, in the case of an ablative laser treatment of the cornea to choose the apex of the cornea by way of outstanding feature and to orient with respect thereto. An orientation with respect to the pupil/iris, as in the state of the art, is also possible with the invention but is not absolutely essential.

The instrument for examining or machining a human eye preferentially further includes components for making available focused treatment laser radiation and for directing the same onto the eye, and also a control arrangement that has been set up to set the focus location of the treatment laser radiation in a manner depending on the signal that is representative of the acquired eye movement.

The present invention consequently makes it possible to take into account, in the course of the treatment of the eye, the position data, gained from the sectional images, pertaining to particular features of the eye and also the eye movements ascertained from the sectional images. In this context, features of the eye may be constituted by, for example, the apex of the cornea, a point on the inside of the cornea, the midpoint of the cornea, the midpoint of the human lens or the fovea (place of best vision).

The interferometric image-acquisition device and the control device may also have been set up to detect a deviation of an actual focus location of the treatment laser radiation from a specified focus location of the treatment laser radiation on or in the eye and to output a notification signal, in which case upon output of the notification signal the control device can, for example, interrupt or stop the emission of the treatment laser radiation onto the eye. According to a further aspect, in accordance with the invention a process for examining or machining a human eye is furthermore provided, including the following steps:

time-resolved acquiring of sectional images of the eye on the basis of three-dimensional optical coherence tomography, ascertaining eye movements solely from the sectional images, and outputting a signal that is representative of the acquired eye movements.

Also in connection with the process aspect, in the course of acquiring the sectional images at least two mutually orthogonal sectional images of the eye can be acquired that each represent a section substantially along the visual axis of the eye.

Furthermore, in the case of the process it is also conceivable that in the course of acquiring the sectional images at least one sectional image of the eye is acquired that represents a section substantially along the margin of the iris of the eye.

It is also conceivable that a plurality of sectional images of the eye are acquired in time-resolved manner and from the sectional images a time-resolved topography of a subregion of the eye is ascertained as the signal that is representative of the eye movement.

The process preferentially includes the following additional steps:

making available focused treatment laser radiation and directing the same onto the eye, and setting the focus location of the treatment laser radiation in a manner depending on the signal that is representative of the acquired eye movements. Alternatively or additionally, the process may include the following step: detecting a deviation of an actual focus location of the treatment laser radiation from a specified focus location of the treatment laser radiation on or in the eye and outputting a notification signal, in which case upon output of the notification signal the emission of the treatment laser radiation is, for example, interrupted or stopped.

BRIEF DESCRIPTION OF THE DRAWINGS

In the following the invention will be elucidated further on the basis of the appended drawings, in which FIG. 2 shows a schematic representation of the human eye in section.

FIG. 3 shows a schematic representation of a centring error as a consequence of a rolling movement of the eye, and FIGS. 4a and 4b show schematic representations relating to the progression of sectional images in the eye.

DETAILED DESCRIPTION OF THE PREFERRED EMBODIMENTS

Figure 1:
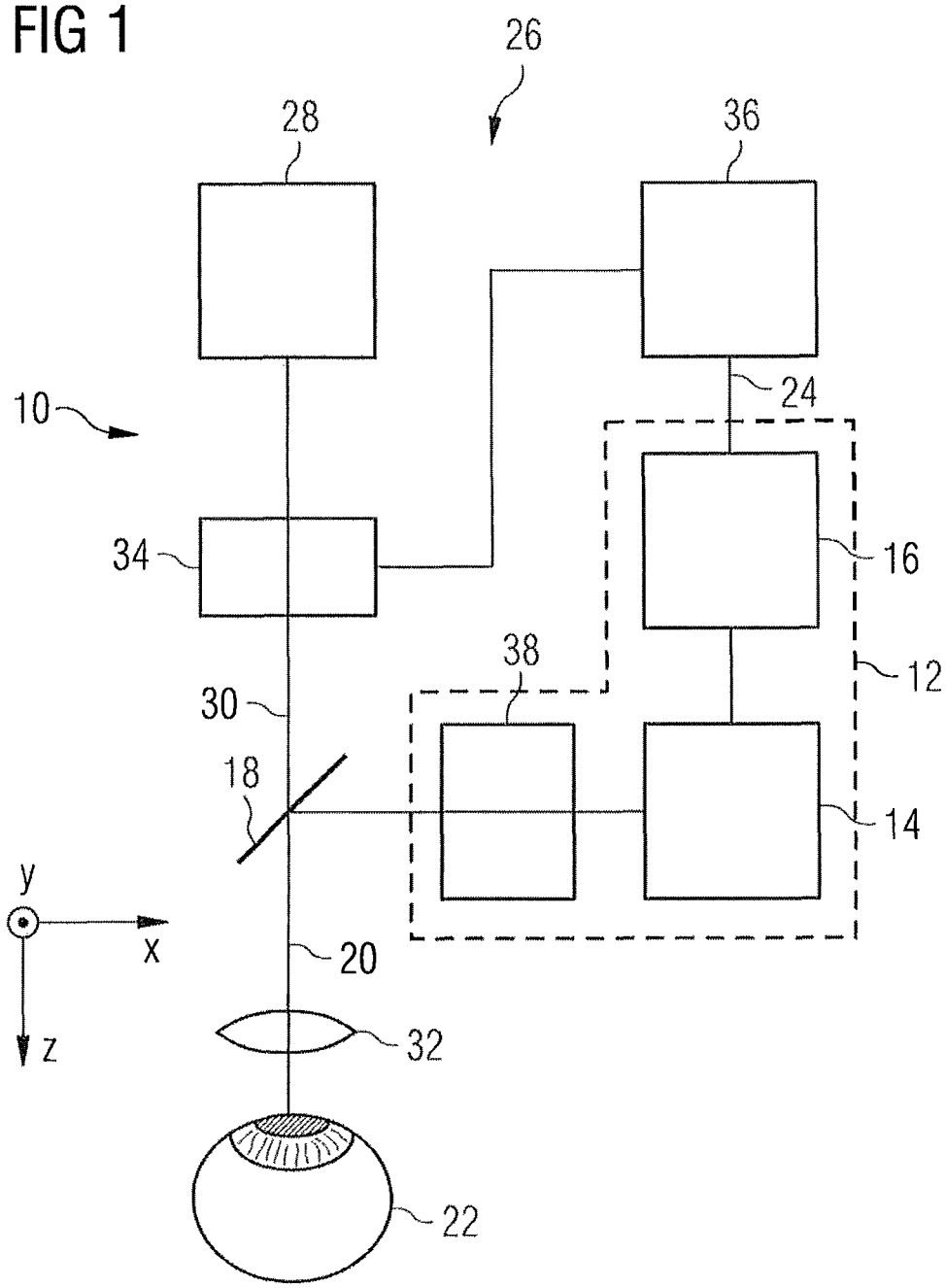
FIG. 1 shows schematically an exemplary embodiment of an instrument for examining or machining a human eye.

FIG. 1 represents, in greatly schematised manner, an exemplary embodiment of an instrument for examining or machining a human eye. The instrument is denoted generally by 10. The instrument includes an eye-tracker 12. The eye-tracker 12 includes an interferometric image-acquisition device 14 and also an evaluating module 16 connected to the image-acquisition device 14. The interferometric image-acquisition device 14 takes the form, for example, of an OLCR measuring device (OLCR: optical low coherence reflectometry) and emits a measuring beam which, by means of a (semitransmitting or dichroic) deflecting mirror 18 or other suitable beam-guiding components, reaches an eye 22 to be treated along an optical beam path 20. The measuring beam emitted by the image-acquisition device 14 passes through a measuring scanner 38 which makes it possible to deflect the measuring beam. Consequently an external as well as internal scanning of the eye 22 by the measuring beam is possible at varying points of the eye tissue. The image-acquisition device 14 causes the generated measuring beam to interfere with a reflected beam coming back from the eye 22. From the measured interference data gained in this way, sectional images of the eye 22 can be acquired in time-resolved manner. The image-acquisition device 14 operates in this case on the basis of two-dimensional or three-dimensional optical coherence tomography. The evaluating module 16 receives data from the interferometric image-acquisition device 14 that include the acquired sectional images, and computes, solely from these sectional images, besides the position and the orientation of the eye in three-dimensional space, also the movements of the eye 22. The eye movements in this case represent translational movements along the three directions in space X, Y, Z as well as rotational movements about the three spatial axes X, Y, Z. A coordinate system which has been drawn in illustrates the three directions in space X, Y, Z, whereby the Z-axis defines the direction of the beam path 20. The eye-tracker 12 yields signals via the interface 24 that are representative of the acquired eye movements.

The instrument 10 further includes a laser-surgical apparatus 26. Said apparatus includes a laser 28 which emits a suitably intense (highly repeating or continuous-wave) laser radiation. The laser radiation propagates along an optical beam path 30 and then impinges on the eye 22 to be treated. In the beam path 30 various components for guiding and shaping the laser radiation are arranged. In particular, these components include a focusing objective 32 as well as a scanner 34 situated upstream of the objective 32, by means of which the focus, generated by the objective 32, of the laser radiation made available by the laser 28 is capable of being deflected along the X-, Y- and Z-directions. A control arrangement 36 controls the scanner 34 in accordance with a predetermined control program which implements an ablation profile to be generated within the eye 22. In the region between the mirror 18 and the eye 22 the measuring beam of the image-acquisition device 14 and the treatment laser beam of the laser 28 run collinearly or at least substantially collinearly. Alternatively or additionally, the laser-surgical apparatus 26 may have been designed in such a manner that the laser 28 takes the form of an ultra-short-pulse laser which emits pulsed laser radiation with pulse durations within the range of, for example, picoseconds, femtoseconds or attoseconds and which is suitable for cutting within the eye tissue, such as is required, for example, for LASIK or in the case of a cataract operation. The laser-surgical apparatus permits, for example, cutting accuracies of ±10 μm or even ±1 μm.

A sectional image of the eye 22 acquired by the image-acquisition device 14 is, for example, represented schematically in FIG. 2. In this picture the apex (i.e. the point furthest removed from the centre of the eye) of the cornea 42, the iris 44, the pupil 46 and the lens 48 can be discerned. In addition, in FIG. 2 an axis 50 has been drawn in which, for example, represents the central (optical) axis of the eye 22 or the visual axis of the eye. In the present case the axis 50 is represented by the position of the apex 40 and the position of the pupillary centre 52.

With a view to the ablation of eye tissue, the appropriate tissue part has to be aligned precisely in position and orientation relative to the instrument 10. However, it cannot be ruled out that during the treatment the eye moves or rotates with respect to the coordinate system X, Y, Z (and consequently with respect to the instrument 10).

Eye-trackers are known in the state of the art that are based on the acquisition of the position of the pupillary centre 52 of the pupil 46 in the eye 22 with the aid of cameras for the purpose of two-dimensional acquisition of the position of the pupillary centre 52 within the X-Y plane. Now if there is provision to ablate eye tissue at a position that is different from the position of the pupillary centre 52, suboptimal treatment outcomes by reason of rotations of the eye may occur, as elucidated in more detail in FIG. 3.

FIG. 3 shows a schematic representation of the pupil 46 and also of the cornea 42 of the eye 22 in the position and orientation thereof within the coordinate system X, Y, Z. The straight line 54 runs in this case parallel to the Z-axis and along the optical beam path 20. Now if eye tissue is to be ablated at the specified position 56 on or within the cornea 42 (for example, after exposing tissue within the cornea by folding aside a tissue lamella (flap) in LASIK, i.e. laser in-situ keratomileusis), a rotary movement of the eye 22 into the orientation of the eye 22 represented by the straight line 60 results in a deviation of the actual position 58 of the ablation relative to the specified position 56 of the ablation if—as in the state of the art—the eye tracking is based merely on a two-dimensional acquisition of the pupillary centre 52. The rotary movement leads in this case to a transverse displacement of the specified position 56 in relation to the actual position 58 along the X- and Z-axes.

An orientation of the ablation procedure with respect to the pupillary centre may therefore be undesirable. On the other hand, an orientation of the ablation procedure may preferably be with respect to the visual axis. The visual axis lies close to the optical axis of the eye and runs approximately through the apex of the cornea and the lens centre of the human lens.

The eye tracking according to the invention is based on the time-resolved acquisition of sectional images of the eye by interferometric image acquisition on the basis of three-dimensional optical coherency tomography. By virtue of the three-dimensional image information the evaluating module 16 can ascertain in time-resolved manner the spatial position and also orientation of the portion of eye tissue to be ablated or of the portion of eye tissue to be machined (e.g. within the scope of a cataract operation) as well as the translational and rotational movements thereof, and on the basis of the interface 24 can communicate a signal that is representative of these data to the control arrangement 36 of the laser 28, in order to set the focus location of the treatment laser radiation in a manner depending on the signal that is representative of the acquired data. Furthermore, for the purpose of controlling the focus location the eye tracking according to the invention may be oriented, for example, with respect to the apex 40, the position of which does not change—in contrast to the pupillary centre 52—in the case of a variable illumination situation. In addition, the invention offers the possibility of choosing from the sectional images an orientation centre for the laser ablation that is positioned close to the tissue to be treated—that is to say, for example, the apex 40 by way of orientation centre for a treatment of the cornea 42. In this case it is expedient to acquire at least two mutually orthogonal sectional images 62, 64 of the eye 22 that each represent a section substantially along the visual axis 50 or some other suitable axis of the eye 22, see FIG. 4a. Alternatively or additionally, it is expedient to acquire at least one sectional image 66 of the eye 22 that represents a section substantially along the margin 68 of the iris 44 (that is to say, the pupillary margin) of the eye 22, see FIG. 4b. A three-dimensional, in particular time-resolved, complete-image acquisition (three-dimensional tomography) consisting of a plurality of sectional images parallel to sectional image 62, a plurality of sectional images parallel to sectional image 64 and/or a plurality of sectional images parallel to sectional image 66 is also conceivable. This complete-image acquisition may, for example, represent a time-resolved 3D topography of the cornea 42, on the basis of which the translational and rotational eye movements can be ascertained and an orientation of the treatment laser radiation with respect to a point in this 3D topography (such as the apex 40 of the cornea 42) is possible.

The invention claimed is:

1. An instrument for examining or machining a human eye, comprising:
   an eye-tracker adapted to acquire eye movements and to output a signal that is representative of the acquired eye movements,
   an interferometric image-acquisition device adapted to acquire a plurality of sectional images of the eye in a time-resolved manner and to operate on the basis of two-dimensional or three-dimensional optical coherence tomography, the sectional images comprising at least one sectional image of the eye that represents a section substantially along the margin of the iris of the eye, the sectional images comprising at least two mutually orthogonal sectional images of the eye, each of the at least two mutually orthogonal sectional images representing a section substantially along a visual axis or an optical axis of the eye to capture the apex of the eye;
   an evaluating module adapted to determine the eye movements comprising movement of the apex from the sectional images; and
   a control arrangement adapted to orient an ablation profile with respect to the apex in response to the movement of the apex.

2. The instrument according to claim 1, further comprising:
   components for providing focused treatment laser radiation and for directing the treatment laser radiation onto the eye; and
   wherein the control arrangement is adapted to set the focus location of the treatment laser radiation in a manner depending on the signal that is representative of the acquired eye movements.

3. The instrument according to claim 1, the interferometric image-acquisition device characterized by a scan rate that is greater than 200,000 line scans per second.

4. The instrument according to claim 1, the interferometric image-acquisition device characterized by a depth range that is greater than 8 millimeters (mm).

* * * * *